United States Patent [19]

Fried

[11] 4,251,732
[45] Feb. 17, 1981

[54] DENTAL X-RAY FILM HOLDERS

[76] Inventor: Alan J. Fried, 1359 Sussex Rd., Teaneck, N.J. 07666

[21] Appl. No.: 67,943

[22] Filed: Aug. 20, 1979

[51] Int. Cl.³ ............................................ G03B 41/16
[52] U.S. Cl. .................................................. 250/479
[58] Field of Search ............................... 250/478, 479

[56] References Cited

U.S. PATENT DOCUMENTS

| 2,005,993 | 6/1935 | Heron | 250/479 |
| 3,356,845 | 12/1967 | Bergendal | 250/479 |
| 4,048,506 | 9/1977 | Updegrave | 250/479 |

Primary Examiner—Craig E. Church

[57] ABSTRACT

An improved dental intra-oral x-ray film packet holding and positioning instrument. Embodiment is of single unit construction. Two diametrically opposed film holding slots are provided for positioning all posterior exposures. Another slot is provided for positioning all anterior and bitewing positions. The slots are so designed that film is held parallel to the long axes of the teeth. An extension for alignment of the x-ray beam with the film is also incorporated in the instrument's unit construction.

3 Claims, 8 Drawing Figures

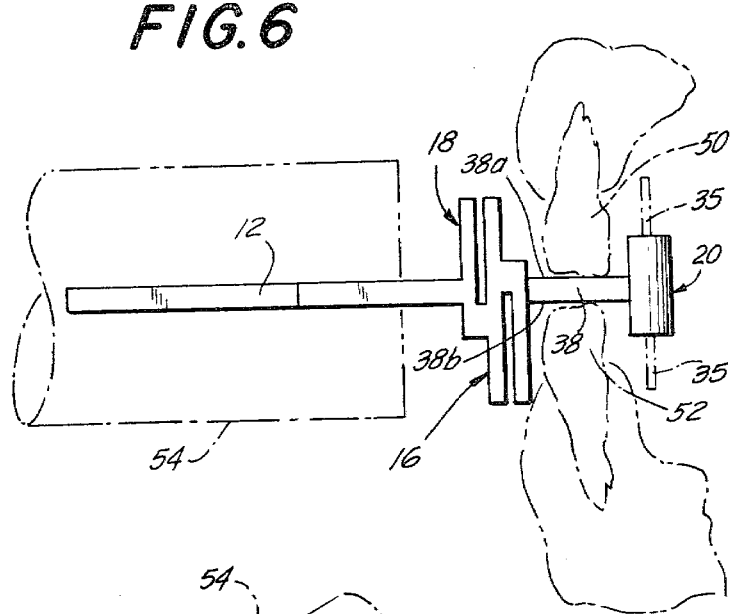
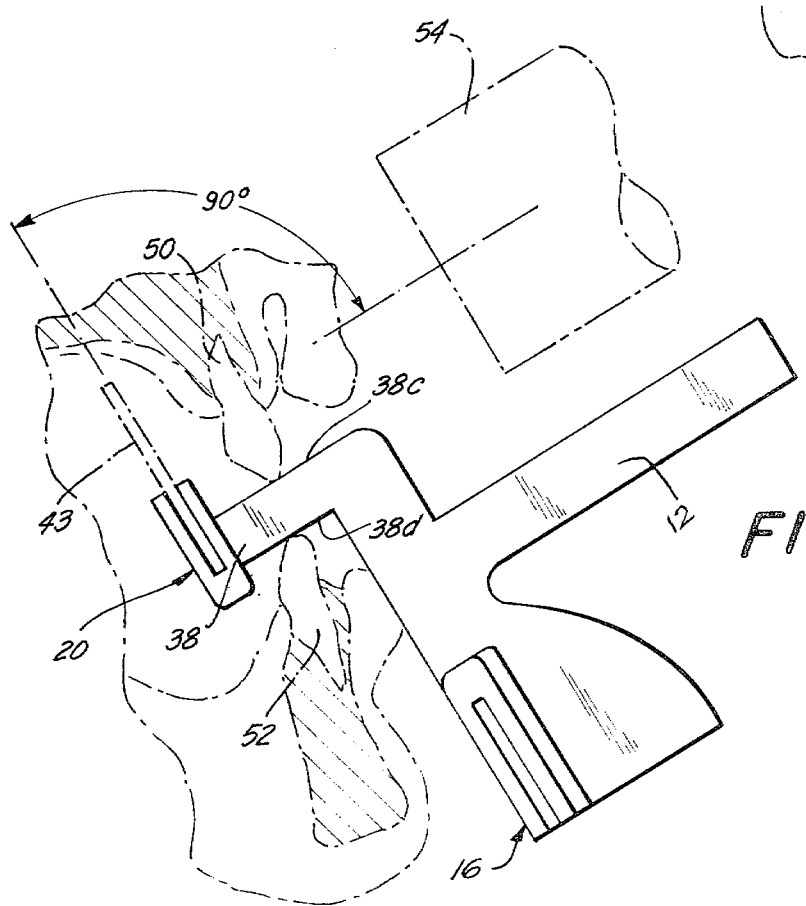

DENTAL X-RAY FILM HOLDERS

A number of instruments of different design are available for holding and positioning dental x-ray film packets in the mouth. Some are effective in holding the film in posterior positions only; some in holding the film in an anterior position only; some require constant changing of parts for positioning of all anterior, posterior and bitewing exposures.

This invention is an improvement in such dental x-ray film holding and positioning instruments. Its embodiment differs from all others in that it is of single unit construction without any other positioning parts, and yet is universally suitable for placing the dental x-ray films intra-orally and taking exposures in all anterior, posterior and bitewing positions with the film parallel to the long axes of the teeth.

The instrument is constructed of plastic or any other suitable radiolucent material and consists of an extension for alignment of x-ray beams, a bite platform and x-ray film holding slotted portions. Because there is no need for adding, removing or changing parts, x-ray exposures can be obtained rapidly, accurately and with simplicity.

SPECIFICATIONS AND DESCRIPTION OF DRAWINGS

FIG. 6 is a fragmentary vertical elevational view of the instrument positioned for taking a right bitewing exposure.

FIG. 7 is a fragmentary vertical elevational view with the instrument positioned for taking an upper anterior exposure.

Figure 1:
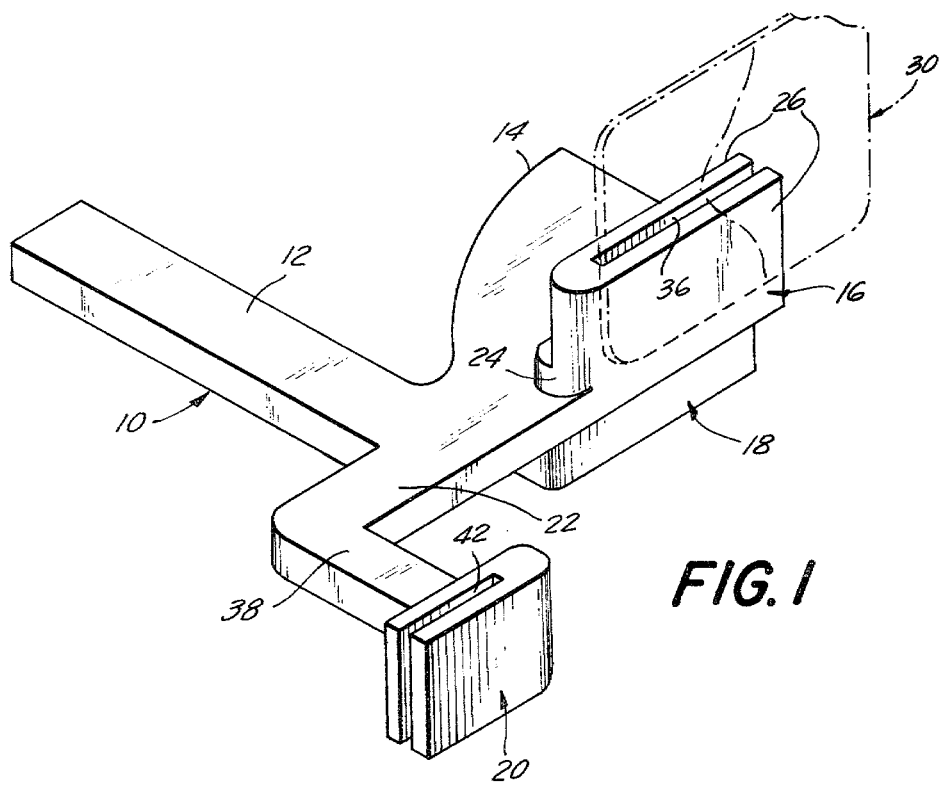
FIG. 1 is an isometric view of the Universal Intra-Oral x-ray film holding and positioning instrument aligned for taking an upper right posterior exposure.

Referring now to FIGS. 1-8, the Universal Intra-Oral x-ray film holding and positioning instrument (10) consists of one-piece construction with an extension (12) for alignment of the x-ray beam, and manual positioning of a bite platform (14) and film holding slotted portions (16), (18) and (20).

The extension (12) is connected to platform (14) at a 'T' shaped area (22). Film holding slotted portion (16), best shown in FIGS. 1, 2, 4 and 6, is perpendicularly connected to platform (14) at (24) and comprises side walls (26) and slot (36) which are used to support film (30) in the upper right posterior exposure position (best shown in FIG. 1) or in the lower left posterior exposure position (best shown in FIG. 2).

Figure 2:
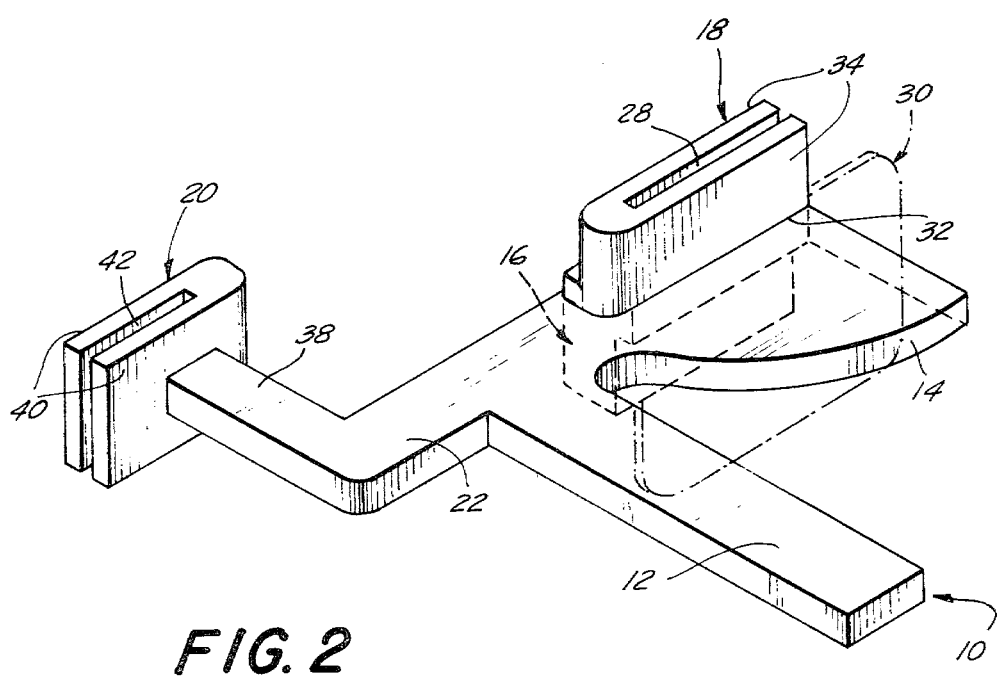
FIG. 2 is an isometric view of the instrument positioned for taking a lower left posterior exposure.

Film holding slotted portion (18) is also perpendicularly connected to platform (14) but is diametrically opposed at (32). FIG. 2 shows film (30) in slotted portion (16). Diametrically opposed is slotted portion (18) with its sidewalls (34) and film holding slot (28).

Figure 4:
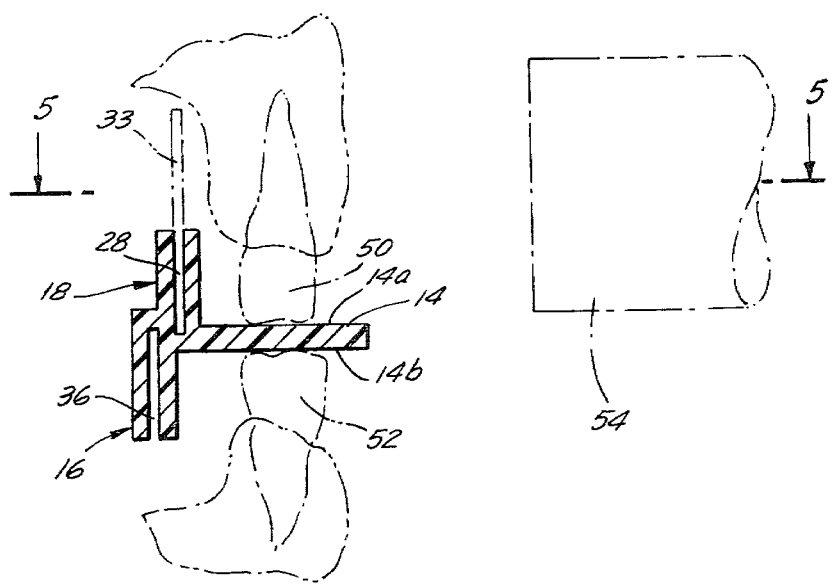
FIG. 4 is a fragmentary vertical sectional view of the instrument positioned for taking an upper left posterior exposure.

FIG. 4 shows film (33) in slot (28) of film holding slotted portion (18) positioned for taking upper left posterior exposure.

Figure 5:
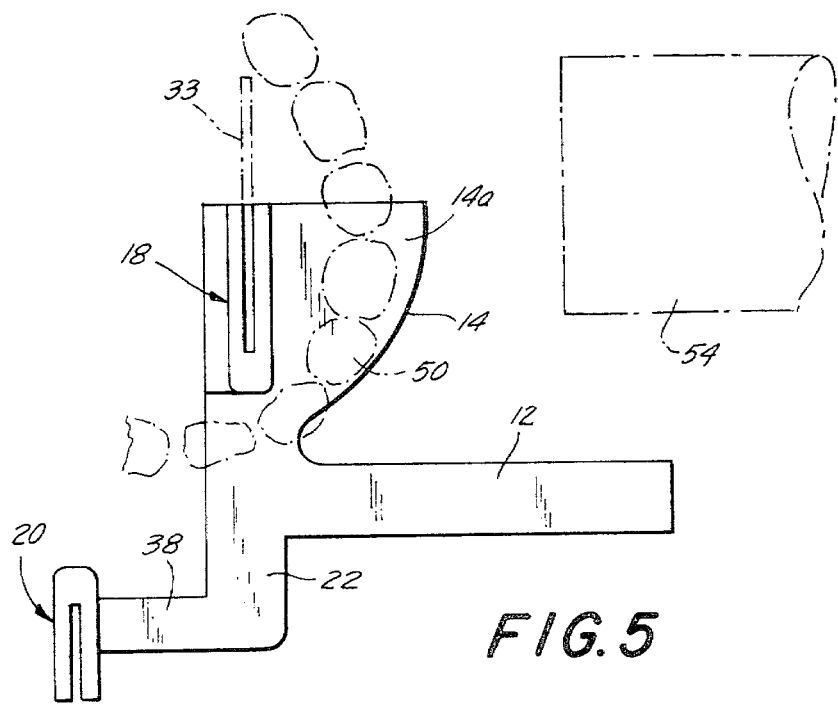
FIG. 5 is a horizontal section taken along line 5—5 of FIG. 4, showing instrument positioned for taking an upper left posterior exposure and x-ray cone alignment with the instrument extension.

FIG. 5 is a view of FIG. 4 seen from line 5—5. The x-ray cone (54) is aligned with film (33) by paralleling it with extension (12).

Figure 3:
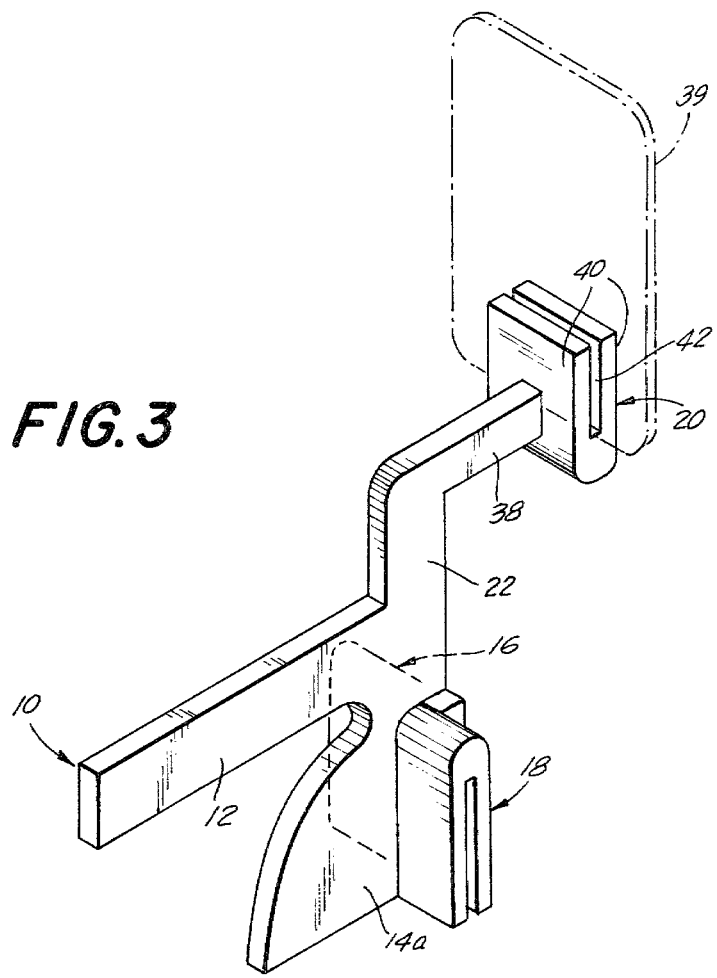
Fig. 3 is an isometric view of the instrument positioned for taking an upper anterior exposure.
Figure 8:
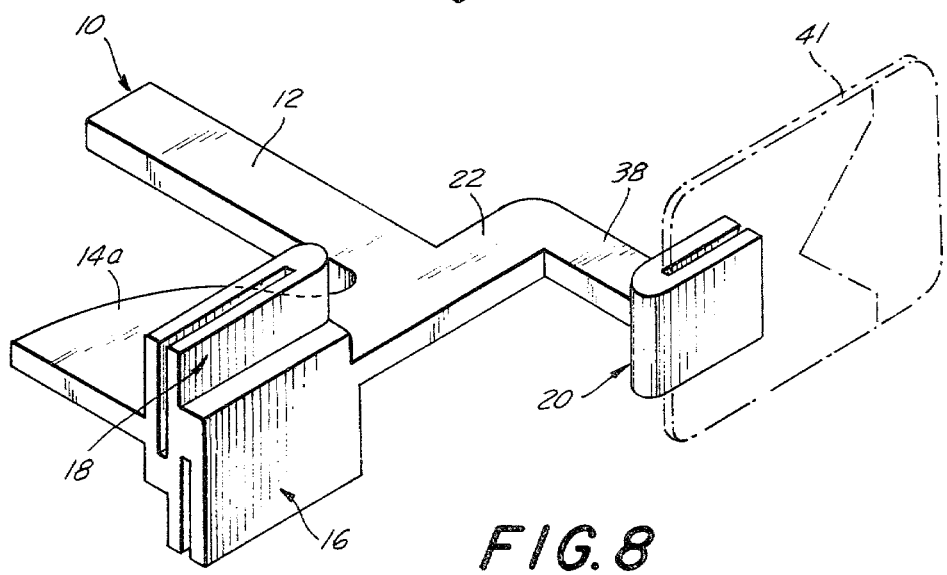
FIG. 8 is an isometric view of the instrument positioned for taking a right bitewing exposure.

Film holding slotted portion (20), (best seen in FIGS. 2, 3, 7 and 8) is connected to the 'T' shaped platform area (22) with a right angle member (38) and comprises sidewalls (40) and slot (42) used to support film in the upper anterior exposure position (39), (best seen in FIGS. 3 and 7). Portion (20) also supports film in the left and right bitewing positions and lower anterior positions. FIG. 8 shows right bitewing exposure position (41).

Referring now to FIGS. 4 and 5, the upper teeth (50) and the lower teeth (52), grip the platform (14) at surfaces (14a) and (14b) and permit directional alignment of x-ray cone (54) with film (33) by paralleling with extension (12) so that x-rays are directed at right angles to film and to teeth (50) in this upper left posterior exposure.

Referring now to FIG. 6, the upper teeth (50) and the lower teeth (52) grip right angle member (38) at edges (38a) and (38b) to permit directional alignment of x-ray cone (54) with extension (12) for right bitewing exposure (35).

Referring now to FIG. 7, the upper teeth (50) and lower teeth (52) grip the right angle member (38) at edges (38c) and (38d) to permit directional alignment of x-ray cone (54) with extension (12) for upper anterior exposure (43). Were the instrument to be rotated 180 degrees along the axis formed by edge (38c), the film holding portion (20) would now position a film for a lower anterior exposure and the x-ray cone (54) would align under rather than over the extension (12). This is best visualized by simply turning FIG. 7 upside down.

Having thus described the invention, what is claimed and desired by Letters Patent is:

1. An instrument for holding and positioning intraoral dental X-ray film packets for all anterior, posterior and bitewing views comprising:

an essentially triangular bite platform having two straight edges forming a right angle and a third curved edge, said bite platform having an upper and a lower biting surface for engagement by upper and lower posterior teeth simultaneously;

slotted film holding means formed by perpendicularly projecting sidewalls at one straight edge of said bite platform, extending above and below the bite platform surfaces, forming two adjacent 'U' shaped slots diametrically opposed to each other so as to provide slotted means for holding a dental X-ray film packet at right angles to either the upper or the lower bite platform surface when taking posterior periapical views;

a relatively long straight narrow extension joining the triangular bite platform at its curved edge side, in a direction perpendicular to the film holding slots, forming a 'T' shaped intersection, said long narrow extension providing means for aligning an X-ray beam source at right angles to the X-ray film packet as it is held in place by the slot of the upper bite surface or as it is held in the slot of the lower bite surface a relatively short straight narrow extension forming a right angle with the 'T' shaped intersection and projecting in a direction 180° opposite to the direction of the X-ray beam alignment extension, said short straight narrow extension forming a bite platform having flat upper and lower biting surfaces suitable for engagement by upper and lower posterior teeth simultaneously; and a 'U' shaped X-ray film holding means joined to the end of said short straight narrow extension, said 'U' shaped means being formed by sidewalls perpendicular to the biting surface of the extension, thereby providing a 'U' shaped slot by which an X-ray film packet can be held at right angles to the X-ray beam alignment extension when the upper and lower posterior teeth engage the biting surfaces of the short straight narrow extension when bitewing views are taken.

2. The instrument of claim 1 wherein said flat upper and lower biting surfaces of the short straight narrow extension are bounded by straight parallel edges, said parallel edges being suitable for engagement by upper and lower anterior teeth simultaneously, thus providing means by which an X-ray film packet is held at 90° to the X-ray beam alignment extension with the film in the 'U' shaped slot when taking upper or lower anterior periapical views.

3. The instrument of claim 1 wherein the straight narrow X-ray beam alignment extension is so positioned at a 'T' shaped intersection between the triangular bite platform and the short narrow extension bite platform that it is always perpendicular to an X-ray film packet held in a 'U' slot of any of the bite platform surfaces.

* * * * *